(12) United States Patent
Bielefeld

(10) Patent No.: US 9,301,842 B2
(45) Date of Patent: Apr. 5, 2016

(54) METHOD AND DEVICE FOR HEART VALVE REPAIR

(71) Applicant: St. Jude Medical, Inc., St. Paul, MN (US)

(72) Inventor: Eric E. Bielefeld, Floyds Knobs, IN (US)

(73) Assignee: St. Jude Medical, Inc., St. Paul, MN (US)

(*) Notice: Subject to any disclaimer, the term of this patent is extended or adjusted under 35 U.S.C. 154(b) by 440 days.

(21) Appl. No.: 13/755,169

(22) Filed: Jan. 31, 2013

(65) Prior Publication Data

US 2014/0214152 A1    Jul. 31, 2014

(51) Int. Cl.
| | |
|---|---|
| *A61F 2/24* | (2006.01) |
| *A61B 17/04* | (2006.01) |
| *A61B 17/00* | (2006.01) |
| *A61B 17/06* | (2006.01) |

(52) U.S. Cl.
CPC ............ *A61F 2/2463* (2013.01); *A61B 17/0401* (2013.01); *A61B 17/0466* (2013.01); *A61B 17/0487* (2013.01); *A61F 2/2466* (2013.01); *A61B 2017/00243* (2013.01); *A61B 2017/0409* (2013.01); *A61B 2017/0414* (2013.01); *A61B 2017/0417* (2013.01); *A61B 2017/0427* (2013.01); *A61B 2017/0464* (2013.01); *A61B 2017/0472* (2013.01); *A61B 2017/0488* (2013.01); *A61B 2017/06052* (2013.01)

(58) Field of Classification Search
CPC ....... A61F 2/2487; A61F 2/2463; A61F 2/24; A61F 2/2427; A61F 2/2466; A61B 17/0401
USPC .................................. 623/2.11, 2.36
See application file for complete search history.

(56) References Cited

U.S. PATENT DOCUMENTS

| | | | | |
|---|---|---|---|---|
| 2005/0119671 | A1* | 6/2005 | Reydel et al. | 606/144 |
| 2005/0251160 | A1* | 11/2005 | Saadat et al. | 606/153 |
| 2009/0118744 | A1 | 5/2009 | Wells et al. | |
| 2009/0163934 | A1 | 6/2009 | Raschdorf, Jr. et al. | |
| 2010/0113873 | A1 | 5/2010 | Suzuki et al. | |

FOREIGN PATENT DOCUMENTS

| | | |
|---|---|---|
| WO | 2007089596 A1 | 8/2007 |
| WO | 2008112237 A2 | 9/2008 |
| WO | 2013003228 A1 | 1/2013 |

OTHER PUBLICATIONS

International Search Report and Written Opinion for Application No. PCT/US2014/012248 dated Jun. 10, 2014.

* cited by examiner

*Primary Examiner* — Victor Nguyen
(74) *Attorney, Agent, or Firm* — Lerner, David, Littenberg, Krumholz & Mentlik, LLP

(57) ABSTRACT

A repair device for repairing a heart valve leaflet in a patient includes a hollow body with a capture tool and a tissue puncture element at the distal end thereof. The capture tool may be used to capture and stabilize the heart valve leaflet tissue. The tissue puncture element may puncture the leaflet tissue and deploy at least one anchor having a length of suture attached thereto. By tensioning the suture, the leaflet tissue may become plicated. The tensioned suture may then be cinched to maintain the plication.

11 Claims, 12 Drawing Sheets

METHOD AND DEVICE FOR HEART VALVE REPAIR

BACKGROUND OF THE INVENTION

Properly functioning heart valves can maintain unidirectional blood flow in the circulatory system by opening and closing, depending on the difference in pressure from one side of the valve to the other. The two atrioventricular valves (mitral and tricuspid valves) are multicusped valves that prevent backflow from the ventricles into the atria during systole. They are anchored to the wall of the ventricle by chordae tendineae, which prevent the valve from inverting.

The mitral valve is located at the gate of the left ventricle and is made up of two leaflets and a diaphanous incomplete ring around the valve, known as the mitral valve annulus. When the valve opens, blood flows into the left ventricle. After the left ventricle fills with blood and contracts, the two leaflets of the mitral valve are pushed upwards and close, preventing blood from flowing back into the left atrium and the lungs.

Mitral valve prolapse is a type of myxomatous valve disease in which the abnormal mitral valve leaflets prolapse (i.e., a portion of the affected leaflet may be billowed, loose, and floppy). Furthermore, the chordae tendineae may stretch and thus become too long, or the chordae tendineae may be ruptured. As a result, the valve is not properly held in a closed condition. As a result of being stretched, the unsupported valve leaflet bulges back, or "prolapses," into the left atrium like a parachute. Thus, as the ventricle contracts, the abnormal leaflet may be propelled backwards, beyond its normal closure line into the left atrium, thereby allowing blood to return to the left atrium and the lungs.

Mitral valve prolapse causes mitral regurgitation. Isolated posterior leaflet prolapse of the human heart mitral valve, i.e. prolapse of a single leaflet, is the most common cause of mitral regurgitation. The exact cause of the prolapse is not clear. Untreated mitral regurgitation may lead to congestive heart failure and pulmonary hypertension.

Despite the various improvements that have been made to devices and methods for mitral valve leaflet repair, there remain some shortcomings. For example, conventional methods of treating mitral valve prolapse include replacement of the mitral valve, clipping the two mitral valve leaflets to one another, and resection of the prolapsed segment using open heart surgery. Such surgical methods may be invasive to the patient and may require an extended recovery period.

Thus, there is a need for further improvements to the current techniques for treating heart valve leaflet prolapse. Among other advantages, the present invention may address one or more of these needs.

BRIEF SUMMARY OF THE INVENTION

The present invention is related to heart valve repair, and specifically to devices, methods and systems for minimally invasive repair of the heart valve leaflet.

One aspect of the present invention provides a repair device for repairing a heart valve leaflet in a patient. One embodiment of the repair device may include an elongated hollow body having a proximal end and a distal end; a capture tool at the distal end of the hollow body, the capture tool being moveable between a retracted position and an extended position; a tissue puncture element at the distal end of the hollow body; at least one anchor adapted to be secured to the heart valve leaflet; and a length of suture connected to the anchor. The anchor may have a sharpened distal tip.

The tissue puncture element may include a hollow tube housing the anchor. The hollow tube may have a sharpened distal tip. Alternatively, the hollow tube may have a blunt tip, and the anchor may have a sharpened distal tip. The repair device may include a plurality of anchors adapted to be secured to the heart valve leaflet, and the hollow tube may house the plurality of anchors.

The tissue puncture element may have an extended position projecting out from the hollow body, and a retracted position within the hollow body. Furthermore, the repair device may include another tissue puncture element at the distal end of the hollow body.

The repair device may include a plurality of anchors adapted to be secured to the heart valve leaflet, and a length of suture connected to each of the plurality of anchors. A single length of suture may be connected to each of the plurality of anchors.

The repair device also may include a cinching member adapted to hold the length of suture in a tensioned condition.

The capture tool may include first and second jaws connected for pivotal movement relative to one another between an open position in which the second jaw is spaced apart from the first jaw, and the closed position in which the second jaw is adjacent the first jaw.

Another embodiment of the repair device may include an elongated hollow body having a proximal end and a distal end; a capture tool at the distal end of the hollow body, the capture tool being moveable between a retracted position and an extended position; an anchor housing tube disposed in the hollow body for sliding movement between a retracted position and an extended position; at least one anchor in the anchor housing tube and adapted to be secured to the heart valve leaflet; and a length of suture connected to the anchor. The anchor may have a sharpened distal tip.

The repair device may include a plurality of anchors in the anchor housing tube and adapted to be secured to the heart valve leaflet, and a length of suture secured to each of the plurality of anchors. A single length of suture may be connected to each of the plurality of anchors, the single length of suture having first and second end portions extending through the hollow body from the distal end toward the proximal end, and an intermediate portion extending between the plurality of anchors.

The repair device may further include a cinching member adapted to hold the length of suture in a tensioned condition. The cinching member may include a pusher and a locking element. The locking element may include a suture lock and an end cap threadedly engaged to the suture lock, the suture lock and the end cap defining a tortuous path therebetween. The tortuous path may be adapted to accommodate the first and second end portions of the suture, wherein threading the suture lock and the end cap closer to one another wedges the first and second end portions of the suture within the tortuous path.

Another aspect of the present invention provides methods for repairing a heart valve leaflet in a patient. Methods according to this aspect of the present invention may include inserting a repair device into the patient to a position adjacent the heart valve leaflet; deploying a first anchor into the heart valve leaflet at a first desired location, the first anchor having a first length of suture attached thereto; deploying a second anchor into the heart valve leaflet at a second desired location spaced from the first desired location, the second anchor having a second length of suture attached thereto; and tensioning the first and second lengths of suture to move the first and second anchors towards one another, whereby a plication is formed in the heart valve leaflet between the first and second desired locations. The first length of suture may be continuous with the second length of suture. Alternatively, the first length of suture may be discontinuous from the second length of suture.

The method may further include applying a cinching member to the first and second lengths of suture to hold the lengths of suture in a tensioned condition.

The step of deploying the first anchor may include deploying the first anchor on a second side of the heart valve leaflet such that the first length of suture passes through the heart valve leaflet to a first side of the heart valve leaflet opposite the second side, and the step of deploying the second anchor may include deploying the second anchor on the second side of heart valve leaflet such that the second length of suture passes through the heart valve leaflet to the first side of the heart valve leaflet.

The method may further include puncturing the heart valve leaflet at the first desired location prior to deploying the first anchor, and puncturing the heart valve leaflet at the second desired location prior to deploying the second anchor. The steps of puncturing the heart valve leaflet at the first desired location and at the second desired location may be performed simultaneously. Furthermore, the puncturing steps may include supporting a second side of the heart valve leaflet and puncturing the heart valve leaflet from a first side toward the second side.

The step of deploying the first anchor may include puncturing the heart valve leaflet at the first desired location with the first anchor, and the step of deploying the second anchor may include puncturing the heart valve leaflet at the second desired location with the second anchor.

The method may further include deploying at least one additional anchor into the heart valve leaflet at a selected location spaced from the first and second desired locations, the additional anchor having an additional length of suture attached thereto, wherein the tensioning step includes tensioning the first, second and additional lengths of suture to move the first, second and additional anchors towards one another, whereby one plication is formed in the heart valve leaflet between the first and second desired locations and another plication is formed in the heart valve leaflet between the second location and the selected location.

The method may further include removing the repair device from the patient and inserting a pusher into the patient to a position adjacent the heart valve leaflet. The tensioning step may include using the pusher to apply a cinching member to the first and second lengths of suture to hold the lengths of suture in a tensioned condition.

DETAILED DESCRIPTION

As used herein, the terms "proximal" and "distal" are to be taken as relative to a user (e.g., a surgeon or an interventional cardiologist) using the disclosed leaflet repair devices. "Proximal" is to be understood as relatively close to the user and "distal" is to be understood as relatively farther away from the user. The invention will be described in connection with the repair of a mitral valve leaflet, but it may be useful in the repair of other types of cardiac valves or in the gathering and clamping of other types of loose body tissue.

Figure 1A:
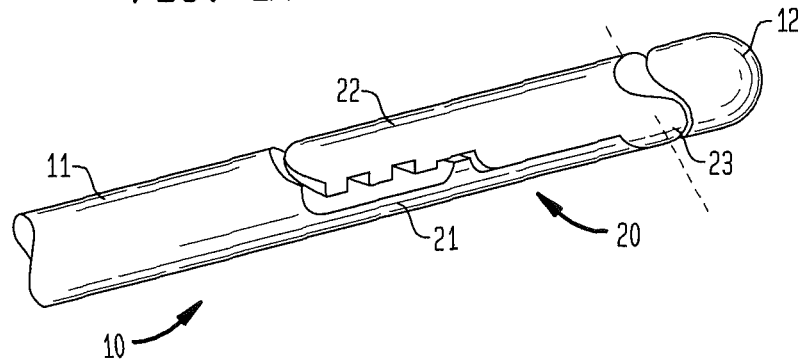
FIGS. 1A and 1B are perspective views of the distal end of a leaflet repair device according to one embodiment of the present invention.
Figure 1B:
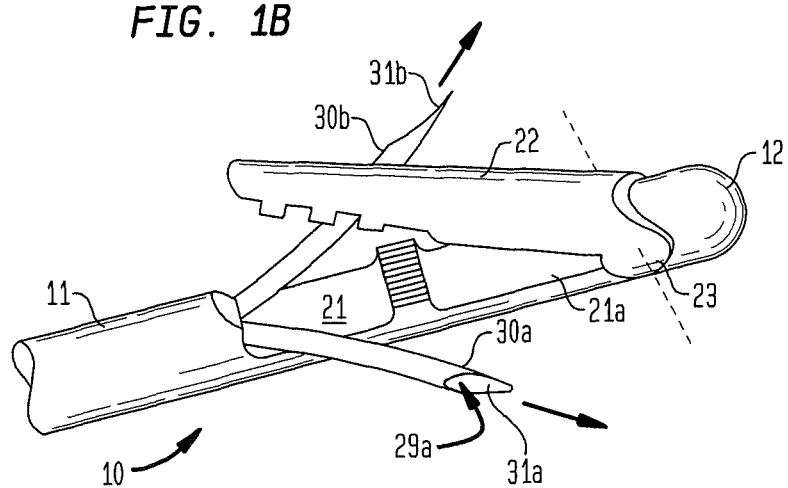
Figure 2:
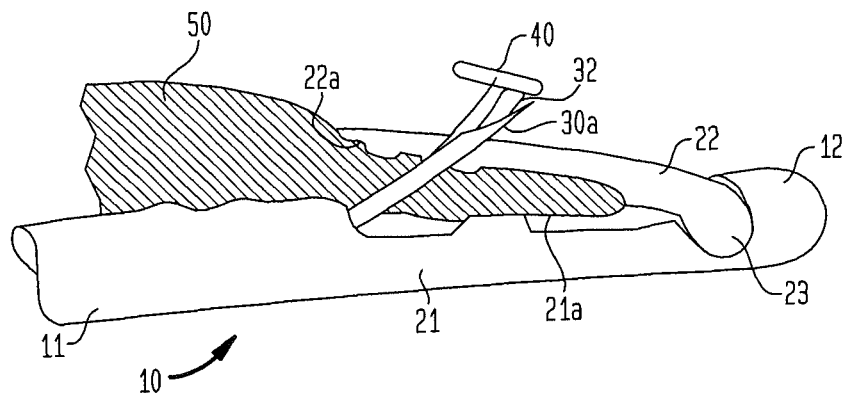
FIG. 2 is a side view of the leaflet repair device of FIGS. 1A and 1B engaged with a heart valve leaflet.

In a first embodiment of the present invention, as illustrated in FIGS. 1A, 1B and 2, a leaflet repair device 10 has a distal end 12 and includes an elongated hollow body 11, a capture tool 20 and at least one tissue puncture element 30 at the distal end of the hollow body 11, both the capture tool and the at least one tissue puncture element being independently moveable between a closed or retracted position and an open or extended position. The hollow body 11 is constructed to be suitable to pass through the vascular system of a human body, and thus may be substantially flexible yet have sufficient strength to move through the vasculature from, for example, the femoral artery or vein up to the heart. The proximal end of device 10 may also include controls, as are known in the art, which remain outside of the human body and which are suitable to guide the distal end portion to the heart, and more specifically, to a particular heart valve leaflet.

The capture tool 20 includes a first jaw 21 fixedly connected to the distal end of the hollow body 11. The fixed jaw 21 may have a surface 21a that is textured or otherwise suitable for gripping and holding leaflet tissue. As illustrated, the fixed jaw 21 and hollow body 11 may be formed integrally with one another. Alternatively, the fixed jaw 21 may be formed separately and joined to the hollow body 11 by known means, such as welding, adhesive, friction fit, or the like. The capture tool 20 also includes a second jaw 22 pivotally connected to the fixed jaw 21 via a hinge joint 23. The hinge joint 23 may be positioned substantially at the distal end 12 of repair device 10, though other configurations suitable for grasping tissue are also envisioned. The pivotable jaw 22 may also have a surface 22a that is textured or otherwise suitable for gripping and holding leaflet tissue. The jaw 22 may pivot between a closed position in which surface 22a is directly opposed to or in contact with surface 21a of jaw 21, and an open position in which surface 22a is spaced apart from surface 21a. For example, the jaw 22 may be in a closed position (FIG. 1A) when travelling through the vascular system, but then may be pivoted to the open position (FIG. 1B) to capture tissue when positioned adjacent a heart valve leaflet 50, all of which will be described below. Since hinge joint 23 is positioned substantially at the distal end 12 of repair device 10, when capture tool 20 is in the open position, the opening between jaws 21 and 22 will face proximally. The movement of jaw 22 may be controlled by a user operating controls on the handle (not shown) of repair device 10. Such controls may include a button or the like for controlling the movement of either an actuation wire, such as that shown in FIG. 5A and discussed further below, or another type of linkage known in the art. Such linkage provides a connection between the jaw 22 and the controls (outside the body of the patient) such that the user's actions can be directed to and operate the jaw 22 (inside the body of the patient).

The tissue puncture element 30a has a lumen 29a extending longitudinally therethrough and may terminate in a sharpened tip 31a at its distal end. For example, the tissue puncture element 30a may be a needle having a tapered tip capable of puncturing tissue. As with the hollow body 11, the hollow structure of the tissue puncture element 30a is sufficiently flexible to pass through the vasculature of the human body while within the hollow body 11, but still has sufficient strength to puncture the heart valve leaflet 50. Further, the distal portion of the element 30a may be flexible and have a pre-bend or the like, such that, as the element 30a extends distally out of the hollow body 11, the distal portion, including sharpened tip 31a, deflects laterally away from hollow body 11, as will be described in greater detail below in connection with the embodiment of FIG. 5A. For example, at least the distal portion of the element 30a may be constructed from a resilient material, such as spring steel, or a shape-memory material, such as nitinol, so that the distal portion will curve as described above when deployed from hollow body 11, but will deflect to a substantially straight configuration when retracted back into the hollow body. The tissue puncture element 30a may be actuated by the user operating controls on the handle of repair device 10. For example, the proximal end of element 30a may be operatively connected to a slide button or other actuator so that movement of the actuator distally extends element 30a out from hollow body 11 and movement of the actuator proximally retracts element 30a back into hollow body 11.

Figure 3A:
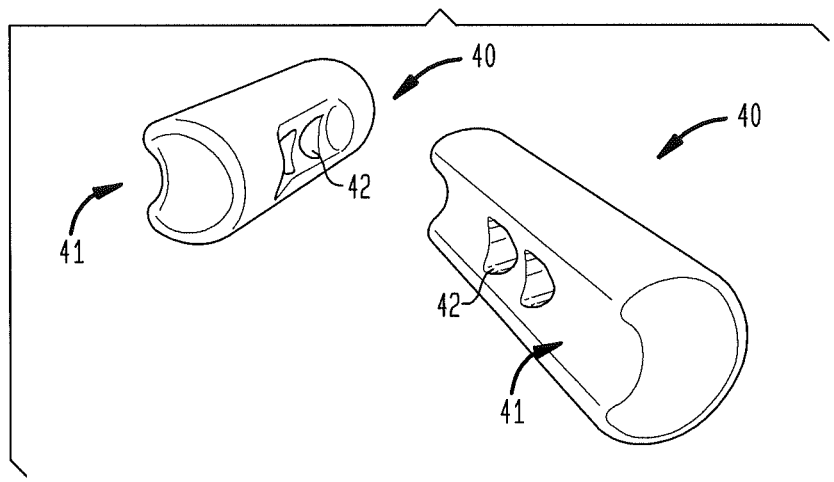
FIGS. 3A-3C are perspective views of an anchor and suture in accordance with one embodiment of the present invention.
Figure 3B:
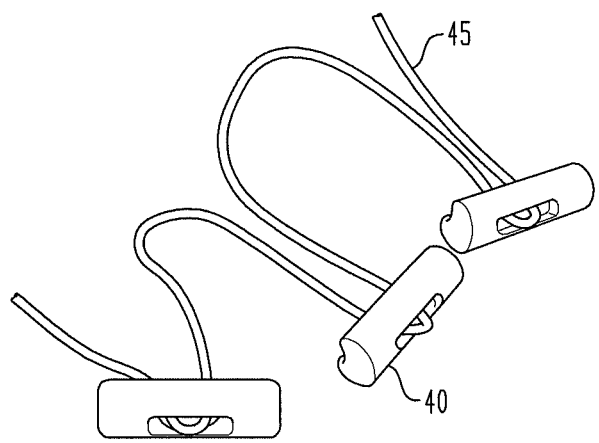
Figure 3C:
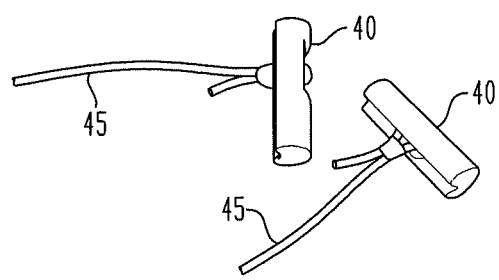

An anchor 40 is positioned, or loaded, within the lumen 29a of the tissue puncture element 30a. As shown in FIGS. 3A-3C, the anchor 40 may have an elongated shape with a transverse cross-section sized to fit within the lumen 29a of the tissue puncture element 30a in a first orientation, but with a length that, with the anchor in an orientation orthogonal to this first orientation, is sufficient to prevent the anchor from pulling back through a puncture in the leaflet. For example, anchor 40 may have a substantially cylindrical body with a channel 41 formed on one side thereof along which a length of suture 45 may be placed when the anchor is positioned within a tissue puncture element 30. The anchor body may have a diameter of, for example, about 0.04 inches, although larger or smaller diameters may be appropriate depending on the leaflet tissue being repaired. The anchor body may have substantially flat ends, which may be beneficial in certain embodiments in which multiple anchors are placed end-to-end in a line within a single tissue puncture element. Of course, the anchor body may have substantially flat ends even if only one anchor 40 is positioned within a tissue puncture element. The anchor 40 may include at least one bore 42 through which the suture 45 may be secured to the anchor.

The suture 45 may extend from the anchor 40 proximally through the lumen 29a of the tissue puncture element 30a and through the hollow body 11. A pushrod 32, or similar device, may reside in the lumen 29a of the tissue puncture element 30a proximally of the anchor 40, and may be pushed distally to discharge the anchor 40. In an alternative arrangement, the suture 45 may extend from anchor 40 distally out from the tip 31a of the tissue puncture element 30a and then proximally along the outside of the tissue puncture element but within the hollow body 11. Whether the suture 45 extends within or alongside the tissue puncture element 30a, it may extend through the length of the hollow body 11 and out from the proximal end thereof for manipulation by the user. In still further arrangements, a plurality of anchors 40 may be positioned within tissue puncture element 30a, secured to a single continuous suture 45 or to individual sutures which are discontinuous from one another.

The device 10 may include a single tissue puncture element 30a, two tissue puncture elements 30a and 30b as shown in FIG. 1B, or more than two tissue puncture elements. Where present, tissue puncture element 30b (and any additional tissue puncture elements) may have substantially the same structure as tissue puncture element 30a (tissue puncture element 30a and tissue puncture element 30b may be referred to individually or collectively as tissue puncture element(s) 30). Further, tissue puncture element 30b may include the same arrangement of anchors 40 and sutures 45 as tissue puncture element 30a, or a different arrangement as the application dictates. When repair device 10 includes two tissue puncture elements 30, the hollow body 11 may have an outer diameter of about 12 F, though other diameters are envisioned so long as the body is capable of passing through the vasculature of a human body. The other structures of this embodiment are dimensioned to properly fit and function within this size of hollow body 11.

The suture 45 may secure to the anchor 40 in any way as necessary. In one example illustrated in FIG. 3B, the suture 45 may pass through the bore or bores 42 of each anchor 40 such that each anchor is secured to, but slidable along, a single suture. In an alternative example, shown in FIG. 3C, each anchor 40 may be secured to an individual suture 45 using a knot or the like.

A cinching member (such as locking element 60 in FIG. 4F, for example) may be provided to secure the suture 45 or sutures in place after deployment of anchor or anchors 40. Any cinching member may be used, such as a washer, suture clip or the like, so long as it maintains tension on the suture or sutures after the procedure has been completed by the user, as will be explained in detail below. Rather than a separate cinching member, the suture or sutures 45 may be secured with a surgical knot, as is known in the art.

FIGS. 4A-4F illustrate a method of repairing a heart valve leaflet 50 using repair device 10. To begin, repair device 10 may be inserted through the vascular system of a human body to a position adjacent to the heart valve leaflet 50. While a transvascular approach is used herein to describe the method of the present invention, other approaches, such as transapical, transseptal, transaortal, or the like may be used. Of course, approaches other than transvascular and particularly transfemoral, would enable hollow body 11 to have a significantly shorter length.

Figure 4A:
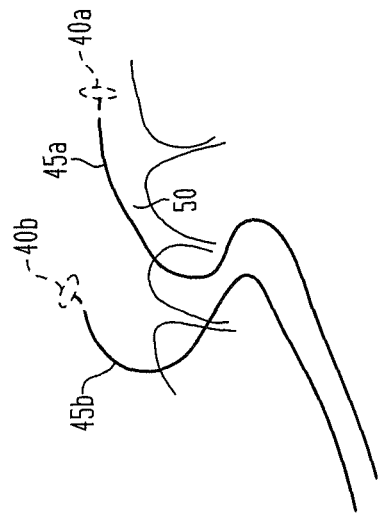
FIGS. 4A-4F are highly schematic views showing a method of repairing a heart valve leaflet using the repair device of FIGS. 1A and 1B.

Once repair device 10 is properly positioned, capture tool 20 may be actuated to pivot jaw 22 to the open position spaced apart from jaw 21. The repair device 10 may then be maneuvered to position jaws 21 and 22 on opposite sides of the leaflet 50, as shown in FIG. 4A, at which point jaw 22 may be pivoted to the closed position to capture the leaflet tissue between the jaws. With the leaflet tissue held securely by the capture tool 20, a first tissue puncture element 30a may be deployed. As the tissue puncture element 30a moves from the retracted position to the extended position, the tip 31a thereof pierces the heart valve leaflet 50 from a first side to create a first puncture aperture at a first location. The anchor 40a may then be deployed from the tissue puncture element 30a to a second side of the leaflet 50 opposite the first side, with the suture 45a extending proximally from the anchor to the first side of leaflet 50 either through the lumen 29a of the tissue puncture element 30a or alongside it. As the user applies tension to the suture 45a, the anchor 40a may rotate on its own to a position flat against the surface of the leaflet 50. The anchor 40a may include a shape, such as an angled side edge, which may assist the anchor in rotating to a position flat against the surface of the tissue. Following deployment of the anchor 40a, the tissue puncture element 30a may be withdrawn to the retracted position within hollow body 11.

Figure 4B:
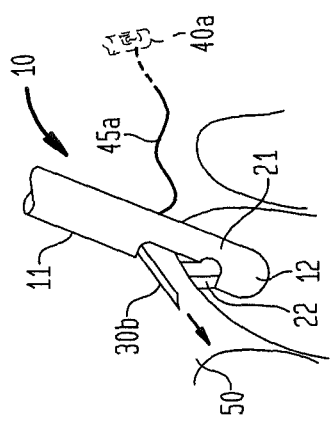
Figure 4C:
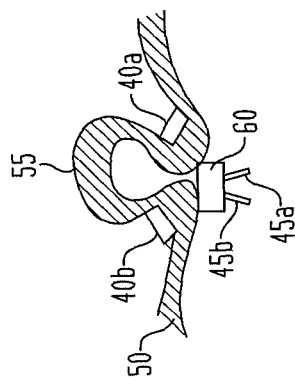

A second tissue puncture element 30b and a second anchor 40b may be deployed either simultaneously with or after the deployment of the first tissue puncture element 30a and first anchor 40a. In either case, the deployment is accomplished in a manner similar to the deployment of the first tissue puncture element 30a and the first anchor 40a, but at a second location spaced apart from the first location, as shown in FIG. 4B. As with the anchor 40a, following deployment the suture 45b will extend from the anchor 40b proximally to the first side of the leaflet 50 either through the lumen 29b of the tissue puncture element 30b or alongside it. The application of tension to the suture 45b causes anchor 40b to rotate to a position flat against the surface of leaflet 50. Sutures 45a and 45b may be separate lengths of suture, each of which may extend to the proximal end of the repair device 10 and to the user. Alternatively, anchors 40a and 40b may be attached to a single length of suture, the ends of which may extend, in similar manner, proximally to the user. Following deployment of the anchor 40b, the tissue puncture element 30b may be withdrawn to the retracted position within hollow body 11.

Figure 4D:
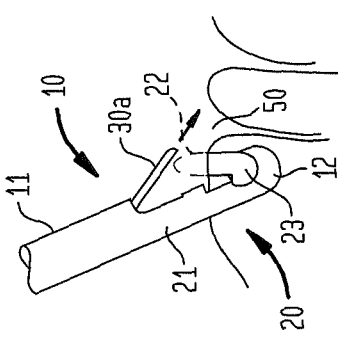
Figure 4E:
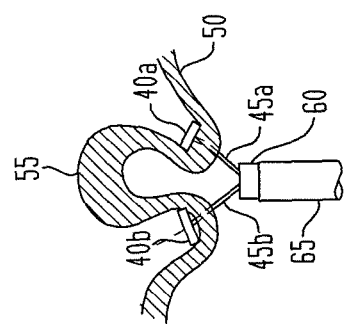
Figure 4F:
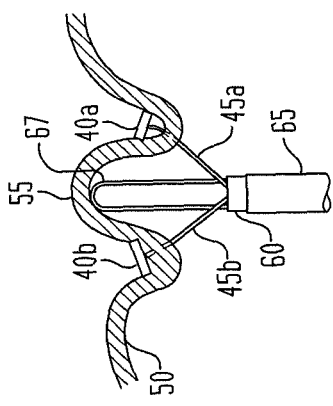

Once the anchors 40a, 40b (and any additional anchors) have been properly deployed and the tissue puncture elements 30 have been moved to their retracted positions, the repair device 10 may be removed from the patient. The ends of sutures 45a, 45b, which extend through hollow body 11 and to the user, may then be threaded through a pusher 65 and locking element 60 such that the pusher and locking element are positioned on the sutures. The pusher 65 may then be inserted into the patient following the same path as repair device 10 to a position adjacent the leaflet 50. The pusher 65 may be inserted independently through a separate catheter (not shown), or through the same catheter as the repair device 10 (following removal of the repair device). In either case, the sutures extending from the anchors would be transferred from the repair device 10 to the pusher 65, as illustrated in FIG. 4D. The pusher 65 may include a plication assistance wire 67 extendable out from the open distal end thereof. Wire 67 may be in the form of a closed loop, a J-hook or other curved shape that presents a blunt end for contacting the leaflet tissue. Extending wire 67 against the leaflet tissue between anchors 40a and 40b, with the anchors held in place by the tension in sutures 45a and 45b, forms a fold or plicated portion 55 of tissue between the anchors. Pusher 65 may then be used to cinch or secure the sutures by placing a cinching element, such as locking element 60, a locking washer, a suture clip, or the like, at a position against the leaflet tissue so as to maintain tension therein. The cinching element will maintain the plication of the leaflet (see FIGS. 4D-4F, for example). The sutures may then be cut proximally of the locking element, and the pusher may be withdrawn from the patient. Optionally, locking element 60 may be omitted and sutures 45a, 45b may be secured against the leaflet tissue using a conventional surgical knot (not shown), which may be advanced and secured using the pusher 65 as a knot pusher.

Alternatively, the tensioning of the sutures 45a, 45b may alone be sufficient to form the plicated portion 55. In this alternative embodiment, the pusher 65 with wire 67 may not be required, and instead a basic knot pusher or the like, as known in the art, may be used to cinch the sutures and secure the plication, after which the suture ends may be cut.

Figure 5A:
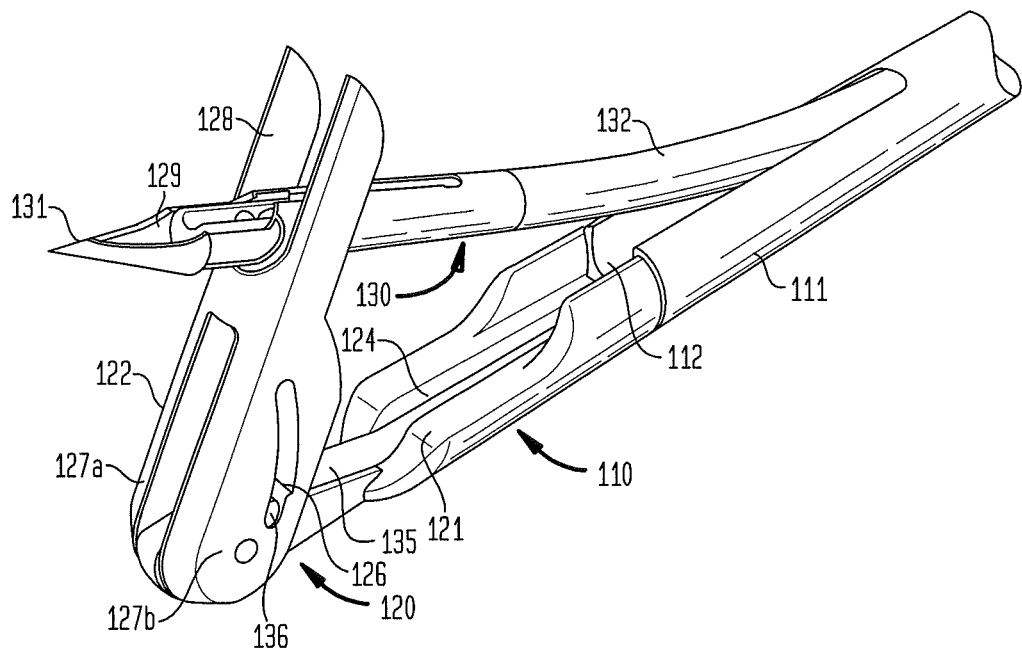
FIGS. 5A and 5B are perspective views of the distal end of a leaflet repair device according to another embodiment of the present invention.
Figure 5B:
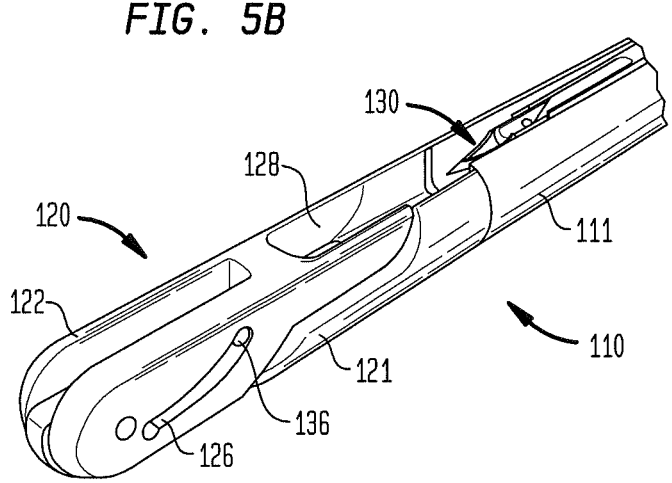

FIGS. 5A-5B illustrate a leaflet repair device 110 in accordance with another embodiment of the present invention. Leaflet repair device 110 includes a hollow body 111 with a capture tool 120 at the distal end thereof. A single tissue puncture element 130 is housed in hollow body 111 rather than the two tissue puncture elements 30a, 30b of device 10 described above. Accordingly, hollow body 111 may have a slightly smaller diameter, about 9 F, than hollow body 11.

Tissue puncture element 130 may have a sharpened tip 131 for piercing leaflet tissue, and a flexible section 132 proximal of the tip. Flexible section 132 may be formed from a shape-memory material, such as nitinol, or may have a shape-memory core. Alternatively, flexible section 132 may be formed from a resilient material, such as stainless steel or a resilient polymer, so as to be curved in a relaxed state. As such, flexible section 132 may be formed with a predetermined curvature that causes tissue puncture element 130 to be deflected laterally away from hollow body 111 during operation of device 110, as will be explained more fully below. The tip 131 and possibly at least a portion of the flexible section 132 may include a lumen 129 to accommodate a plurality of anchors, as illustrated in FIG. 5A. Suitable anchors may include anchors 40 illustrated in FIGS. 3A-C. Capture tool 120 includes a first member 121 fixedly connected to the distal end of hollow body 111, and a jaw 122 pivotally connected to the fixed member at the distal end of device 110. Jaw 122 may be actuated independently of tissue puncture element 130 between a closed position (FIG. 5B) and an open position (FIG. 5A) in which the opening between the jaw 122 and the fixed member 121 faces proximally. The operation of jaw 122 may be controlled by an actuation wire 135 disposed for sliding movement through hollow body 111 and through a channel 124 formed in the fixed member 121 of capture tool 120. The proximal end of actuation wire 135 may extend to the proximal end of repair device 110 for operation by a user. At its distal end, actuation wire 135 includes an arm 136 arranged at substantially a right angle to the length of the actuation wire. The ends of arm 136 are disposed in curved slots 126 formed in the longitudinal sidewalls 127a, 127b of jaw 122. The orientation and curvature of slots 126 are such that the slots produce a camming action, whereby movement of arm 136 from the proximal end of the slot toward the distal end thereof causes jaw 122 to move from the closed position to the open position, and movement of the arm from the distal end of the slot toward the proximal end thereof causes the jaw to move from the open position to the closed position. Jaw 122 may include a fork 128 on its free end which, when the jaw is in the closed position, is open in the proximal direction. Fork 128 is sized to receive the tip 131 of tissue puncture element 130.

Figure 6:
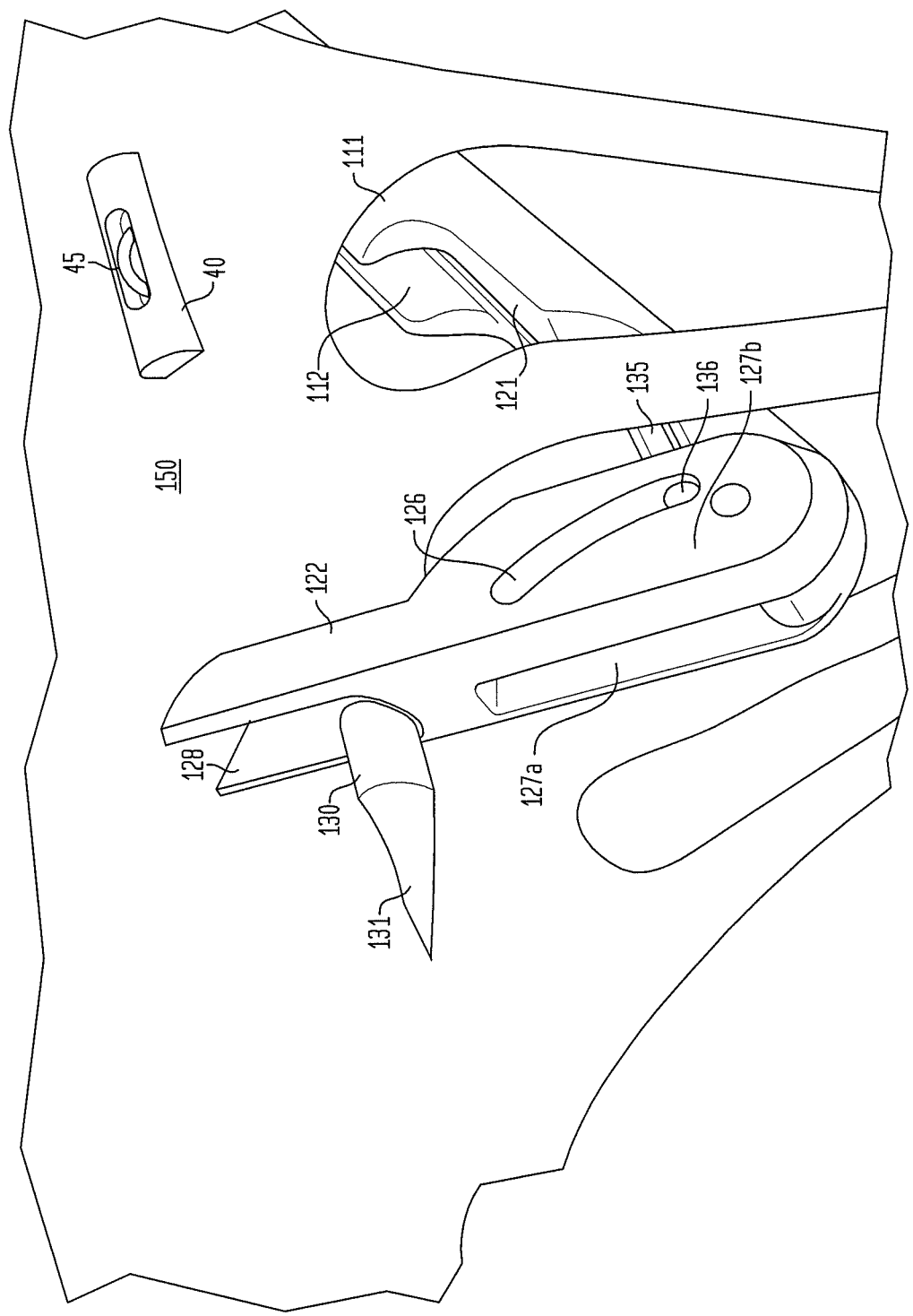
FIG. 6 is a highly schematic perspective view showing a method of repairing a heart valve leaflet using the repair device of FIGS. 5A and 5B.

The use of device 110 to repair a heart valve leaflet will now be described. Similar to the use of device 10 described above, with tissue puncture element 130 in the retracted position and jaw 122 in the closed position, repair device 110 is inserted through the vascular system of the patient until the distal end of the device, including capture tool 120, is positioned adjacent to and in front of or on the proximal side of, the heart valve leaflet tissue, as shown in FIG. 6. The jaw 122 is then moved to the open position by sliding actuation wire 135 distally to move arm 136 distally through slots 126. Repair device 110 may then be manipulated to position jaw 122 behind, or on the distal side of, the heart valve leaflet tissue. In other words, the heart valve leaflet tissue will be located between fixed member 121 and open jaw 122.

With jaw 122 positioned behind the leaflet tissue 150, the tissue puncture element 130 may be moved distally to the extended position. As the tissue puncture element 130 moves distally, the shape bias of the flexible section 132 will cause it to flex laterally away from hollow body 111. In this regard, the proximal end of fixed member 121 and a distal portion of hollow body 111 may be formed with an elongated channel 112 that provides clearance to accommodate the lateral movement of tissue puncture element 130 away from the hollow body. As tissue puncture element 130 continues to move distally, tip 131 will eventually pierce the leaflet tissue 150 at a position between the tines of fork 128. With the tip 131 of tissue puncture element 130 extending through the leaflet tissue 150 and through the fork 128 at this first desired position, a first anchor 40 may be deployed on the distal side of the leaflet tissue, with a suture 45 connected to the anchor extending through the leaflet tissue to the proximal side thereof.

Device 110 may then be prepared for removal from this first puncture site by withdrawing tissue puncture element 130 to its retracted position and returning jaw 122 to its closed position by pulling actuation wire 135 proximally. Device 110 may then be moved from this first puncture site to a second desired position, leaving the first anchor 40 in place, as shown in FIG. 6. The procedure described above may then be repeated to deploy a second anchor 40 at the second desired position. This procedure may be repeated as many times as may be necessary to deploy the number of anchors desired.

Once all of the anchors 40 have been deployed, the suture or sutures 45 from each anchor may be tensioned by the user and secured to complete the plication of the leaflet tissue. The suture or sutures 45 may be secured using any of the arrangements described above in connection with device 10 to maintain the plication of the leaflet tissue.

Figure 7:
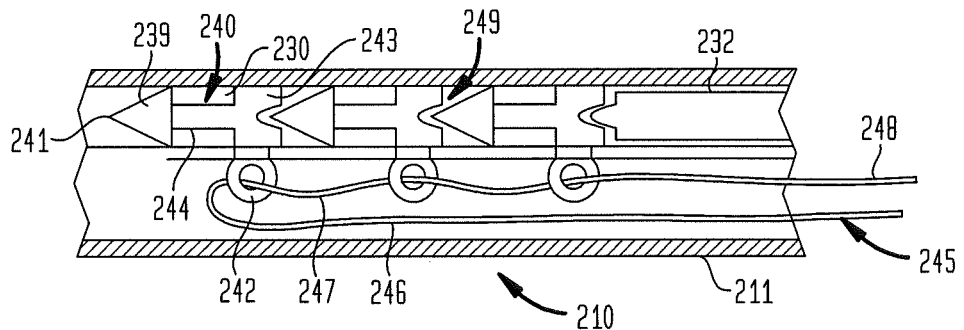
FIG. 7 is a longitudinal view in partial cross-section of a distal portion of a leaflet repair device according to a further embodiment of the present invention.
Figure 8A:
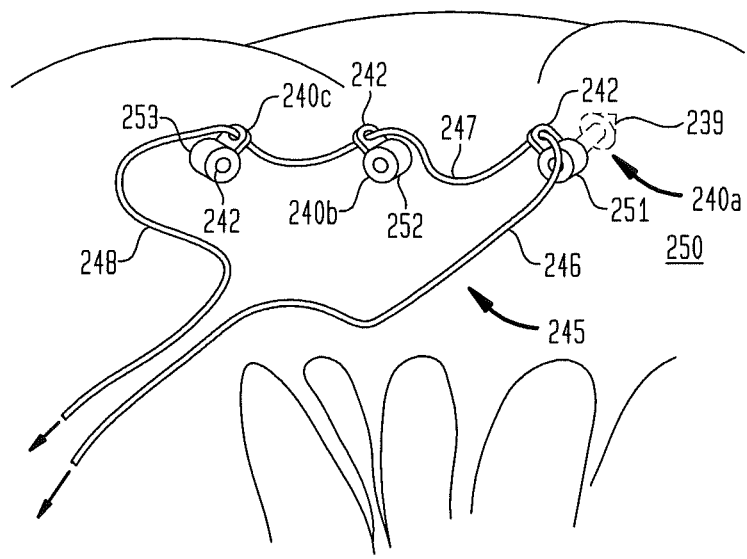
FIGS. 8A-8B are highly schematic views showing a method of repairing a heart valve leaflet using the repair device of FIG. 7.
Figure 8B:
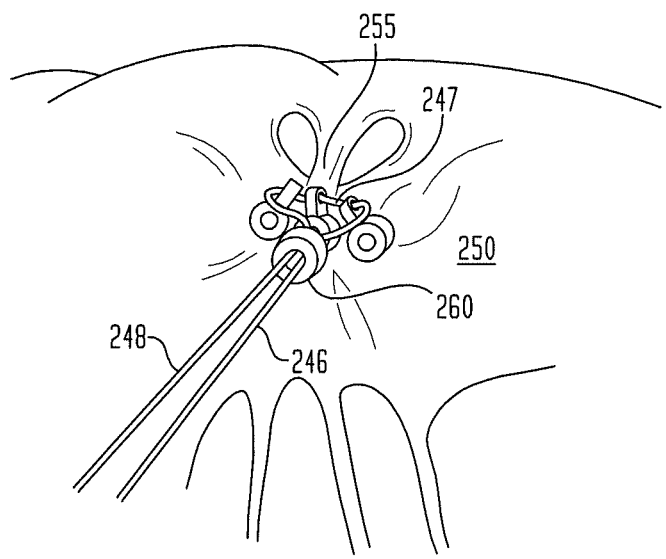
Figure 9A:
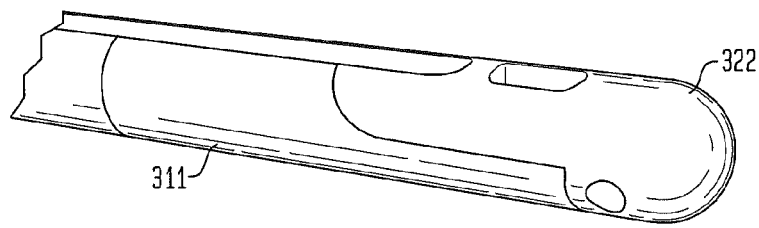
FIGS. 9A-9B are perspective views of the distal end of a leaflet repair device according to still another embodiment of the present invention.
Figure 9B:
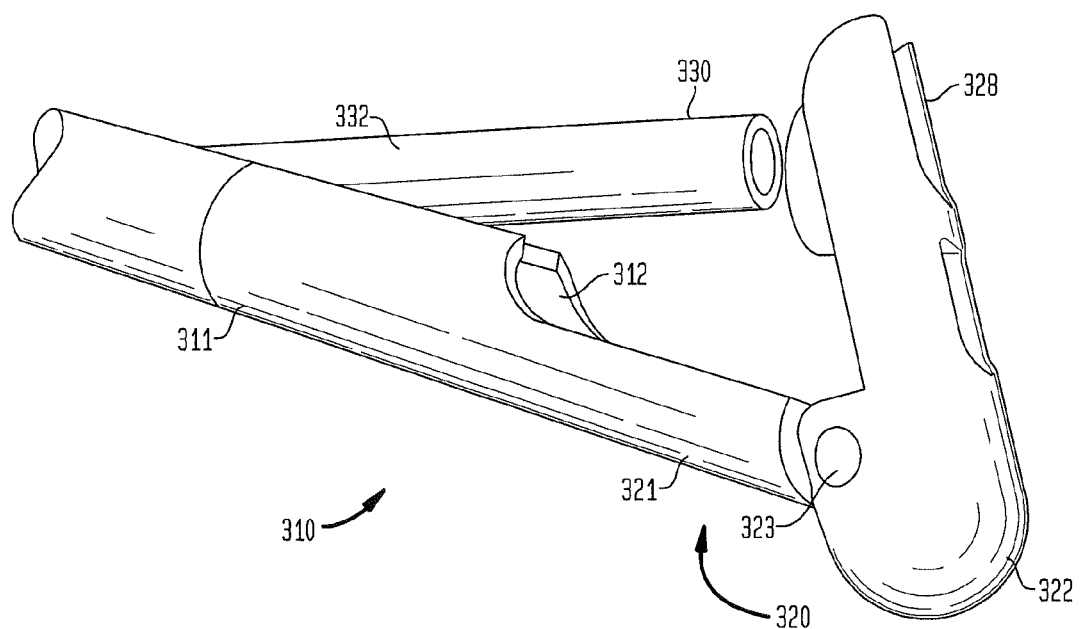
Figure 9C:
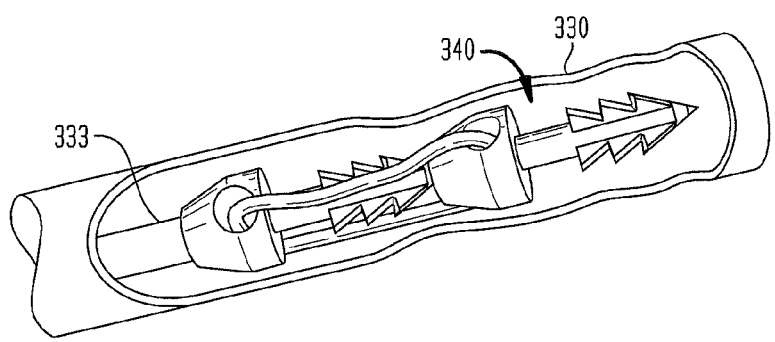
FIG. 9C is a longitudinal view in partial cross-section of the distal end of the leaflet repair device of FIGS. 9A and 9B.

FIGS. 7 and 8A-8B illustrate a leaflet repair device 210 in accordance with a further embodiment of the present invention. The leaflet repair device 210 includes an elongated hollow body 211, which has an anchor housing tube 230 therethrough and a length of suture 245 having at least one anchor 240 secured thereto. Repair device 210 may optionally also include a capture tool (such as capture tool 20 illustrated in FIGS. 1A-B and discussed above, or capture tool 320 illustrated in FIGS. 9A-B and discussed below) extending from a distal portion of hollow body 211.

The anchor or anchors 240 of this embodiment may be different from anchors 40 described above. Thus, anchors 240 may have a generally cylindrical body 243 with a narrowed shaft 244 extending from the distal end thereof. A conical tip 239 with a sharpened point 241 may be provided at the other end of shaft 244, and a tab having an eyelet 242 or other structure for receiving the suture 245 may extend from body 243. At its proximal end, body 243 may be formed with a recess 249 shaped to receive the point 241 of a next adjacent anchor 240. As a result, anchors 240 may be positioned within the anchor housing tube 230 such that each anchor nests in line with the other anchor or anchors adjacent to it, as illustrated in FIG. 7. The anchor or anchors 240 may be deployed from the tube 230 using a pushrod 232 or the like, which may extend from a proximal end of tube 230, where it may be maneuvered by the user, to a distal end of the tube at which anchors 240 are positioned for deployment. The user may advance the pushrod 232 distally to deploy one anchor 240 at a time.

The length of suture 245 may include a first portion 246 extending through the elongated catheter assembly to the first anchor 240, a middle portion 247 extending through the eyelets 242 in each of the anchors, and a third portion 248 extending from the final anchor through the elongated catheter assembly. A cinching member may be provided to secure the suture 245 in place after deployment of anchor or anchors 240. Any cinching member may be used, such as a locking element (260, FIG. 8B), washer, suture clip or the like, so long as it maintains tension on suture 245 after the procedure has been completed by the user. Rather than a separate cinching member, the suture 245 may be secured with a surgical knot as is known in the art.

The use of device 210 to repair a heart valve leaflet will now be described with reference to FIGS. 8A-8B. As with the other embodiments discussed above, the repair device 210 is inserted through the vascular system of the patient until the distal end of the device (portion shown in FIG. 7) is positioned adjacent to the heart valve leaflet tissue 250. The capture tool (not shown) may then be opened and positioned with the fixed member on one side of the leaflet tissue and the movable jaw on the other side of the leaflet tissue. The user may then position the distal end of hollow body 211 against the leaflet tissue 250 and advance the pushrod 232 in the distal direction to expel an anchor 240a from tube 230, such that the sharpened point 241 of the anchor presses against and punctures the tissue at the first desired location 251. Anchor 240a is advanced until the entirety of conical tip 239 is pushed through the leaflet tissue 250 and resides on the back side of the leaflet tissue.

With the conical tip 239 of the first anchor 240a secured through the tissue 250 at the first desired location 251, the capture tool may be returned to its closed position and device 210 may be moved to a second desired location 252. The procedure described above may then be repeated to deploy a second anchor 240b at the second desired location 252. This procedure may be repeated as many times as may be necessary to deploy the number of anchors desired, such as the three anchors 240a, 240b, 240c shown in FIG. 8A (anchor 240c, for example, would be positioned at the third desired location 253). As illustrated, the suture 245 may pass through the eyelets 242 of each of the anchors 240 such that the three anchors are secured to and slidable along the same length of suture.

Once all of the anchors 240 have been deployed, the suture 245 may be tensioned by the user and secured to form a plicated portion 255 of the leaflet tissue 250, as illustrated in FIG. 8B. In one example, the user may tension the first portion 246 and the third portion 248 of suture 245 to draw anchors 240 towards one another and form the plicated portion 255 of the leaflet tissue. Tensioning of suture portions 246 and 248 causes the middle portion 247 of the suture to slide through the eyelets 242 of the anchors, drawing them together. The suture 245 may then be secured using any of the cinching members or other arrangements described above, such as locking member 260, to maintain the plication of the leaflet tissue. The suture ends may then be cut and the suture, anchors and cinching member securely maintain the plication.

It will be appreciated that repair device 210 eliminates the need for a separate tissue puncture element having a sharpened tip as in the embodiments described above. Rather, repair device 210 deploys anchors 240 from an anchor housing tube 230 having a blunt distal end, and uses the sharpened points 241 of the anchors to pierce the leaflet tissue 250. Moreover, it is contemplated that repair device 210 may be provided without a capture tool. In such event, anchors 240 would press against and pierce the leaflet tissue 250 without the assistance of a capture tool to stabilize the tissue and hold it in place.

FIGS. 9-14 illustrate a leaflet repair device 310 in accordance with another embodiment of the present invention. In repair device 210 described above, the entirety of conical tips 239 protrude through the leaflet tissue 250, such that the exposed points 241 could damage surrounding tissue. Leaflet repair device 310 includes anchors 340 designed to minimize the possibility of damaging surrounding tissue. Leaflet repair device 310 includes a hollow body 311 with a capture tool 320 at the distal end thereof. Within hollow body 311 is an anchor housing tube 330 in the form of a hypotube within which at least one anchor 340 may be located (see FIG. 9C).

The capture tool 320 includes a first member 321 fixedly connected to the distal end of hollow body 311, and a jaw 322 pivotally connected to the fixed member by a pin 323. The jaw 322 and fixed member 321 may be constructed of stainless steel or a like material. Jaw 322 may be actuated between a closed position (FIG. 9A) and an open position (FIG. 9B) in which the opening between the jaw and the fixed member faces proximally. Jaw 322 may be operated by an actuation wire (not shown) in a manner similar to the operation of capture tool 120 described above. Jaw 322 may include a fork 328, on its free end which, when the jaw is in the closed position, is open in the proximal direction. Fork 328 is sized to receive between its tines the tissue-piercing distal end 341 of an anchor 340.

The anchor housing tube 330 includes a flexible section 332 along at least a portion spaced from the distal end thereof. Flexible section 332 may be formed from a shape-memory material, such as nitinol, or may have a shape-memory core. Still further, flexible section 332 may be formed from a resilient metal or polymer so as to be curved in a relaxed state. As such, flexible section 332 may be formed with a predetermined curvature that causes the tube 330 to be deflected laterally away from hollow body 311 during operation of device 310, as will be explained more fully below. The anchor housing tube 330 has a retracted position (FIG. 9A) within hollow body 311, and an extended position (FIG. 9B) projecting away from the hollow body.

Figure 10A:
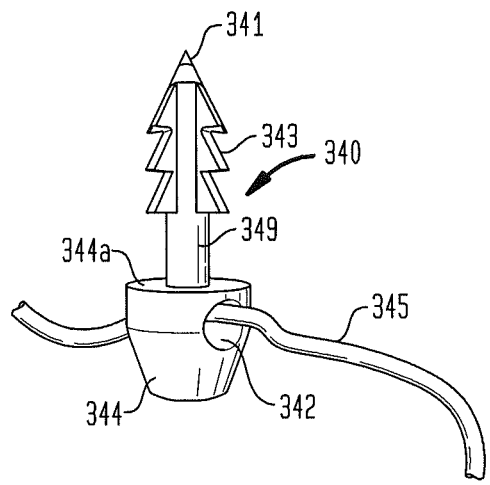
FIGS. 10A and 10B are perspective views of an anchor and suture in accordance with another embodiment of the present invention.
Figure 10B:
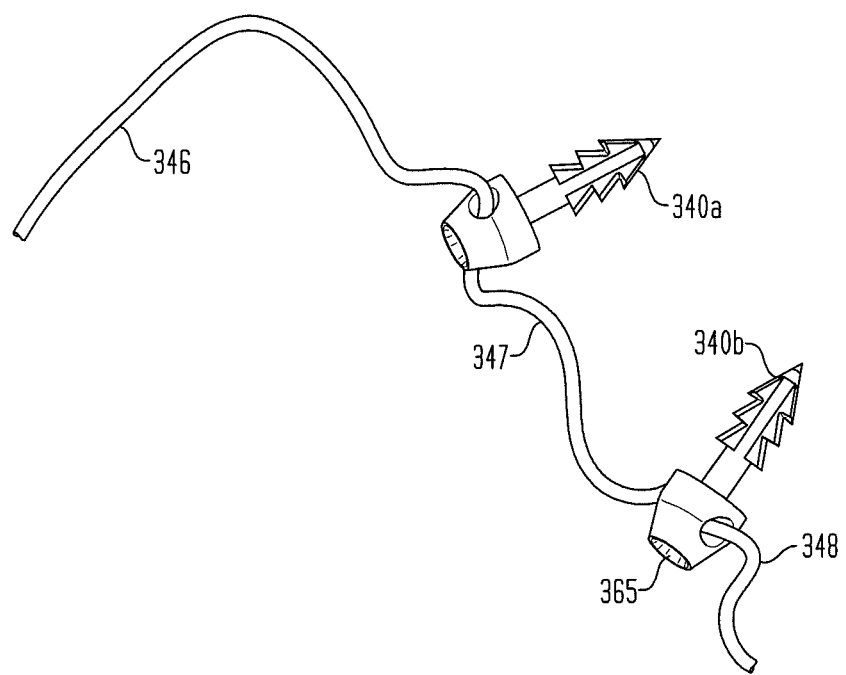

The anchor housing tube 330 accommodates one or more anchors 340 (see FIG. 9C) and a suture 345 associated therewith. The anchors 340 of this embodiment are similar to anchors 240 described above, but have been specifically designed to not penetrate entirely through the thickness of leaflet tissue 250. FIGS. 10A and 10B illustrate further details of the anchors. Anchors 340 may have a generally cylindrical body 344 with a shaft 349 extending from the distal end thereof. Shaft 349 may have a sharpened point 341 and one or more barbs 343 between the point and body 344. The length of shaft 349 from body 344 to sharpened point 341 preferably is less than the thickness of leaflet tissue 250. In an exemplary embodiment, body 344 may have an outer diameter of about 0.05 inches and shaft 349 may have a length of about 0.10 inches. Of course, these dimensions may differ to best suit anticipated parameters of a surgery or surgical site. Additionally, at its juncture with shaft 349, body 344 has an enlarged flat face 344a that, as will be described below, acts as a stop to prevent shaft 349 from penetrating further into leaflet tissue 250. At its proximal end, body 344 may include a recess 365 shaped to receive the sharpened point 341 of a next adjacent anchor 340. Recess 365 enables anchors 340 to be positioned within anchor housing tube 330 in a nested relationship.

The anchor or anchors 340 may be deployed from tube 330 using a pushrod 333 or the like. Pushrod 333 may extend from a proximal end of tube 330, where it may be maneuvered by the user, to a distal end of the tube at which anchors 340 are positioned for deployment. The user may advance the pushrod 333 distally to deploy one anchor 340 at a time.

A transverse aperture 342 through body 344 may be sized to receive suture 345. Suture 345 is a single length of suture which may include a first portion 346, a middle portion 347, and a third portion 348. The first portion 346 may extend through hollow body 311 to the first anchor 340, and the third portion 348 may extend from the final anchor 340 through hollow body 311. Between the first portion 346 and the third portion 348, the middle portion 347 of suture 345 may extend through the apertures 342 in each of the anchors 340 to link them to one another.

Figure 13A:
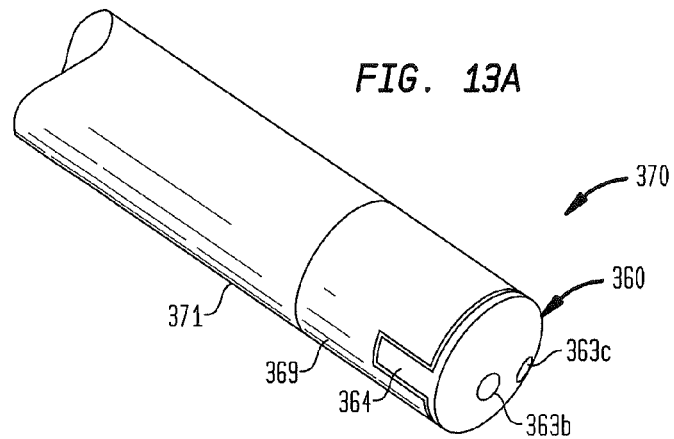
FIG. 13A is a perspective view of the distal end of a suture lock according to the present invention.
Figure 13B:
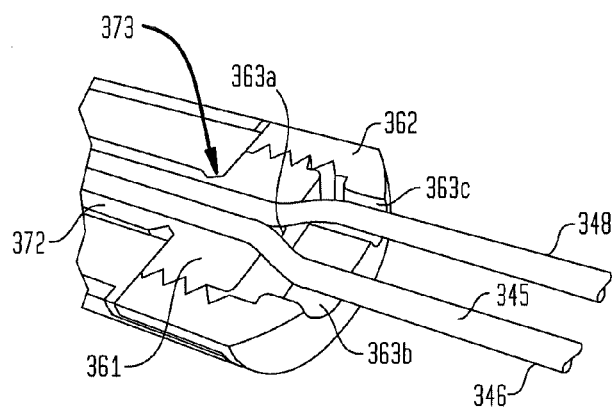
FIG. 13B is a longitudinal cross-sectional view of the suture lock of FIG. 13A, with the suture assembled therein.
Figure 13C:
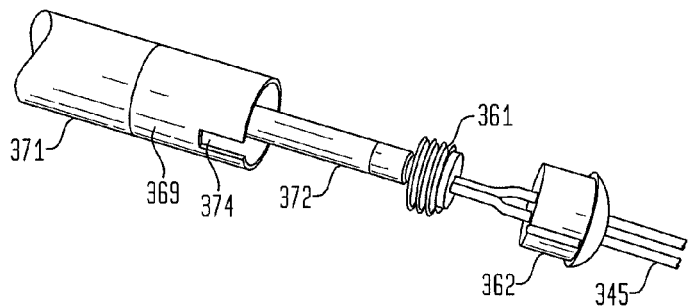
FIG. 13C is an exploded view of the suture lock of FIG. 13A with the suture assembled therein.

Leaflet repair device 310 may further include a pusher 370, as illustrated in FIGS. 13-14, which may be used to tension and secure suture 345 in place to create and maintain a plication in the heart valve leaflet. The pusher 370 may include a catheter 371 which may have a diameter of, for example, about 0.085 inches. A locking mechanism 360 on the distal end of catheter 371 may include a suture lock 361 with outer or male threads, and an end cap 362 with inner or female threads for joining the end cap to the suture lock. Suture lock 361 may have an axially oriented through bore 363a sized to receive two lengths of suture 345 in side-by-side relationship, and end cap 362 may include a pair of apertures 363b and 363c spaced from one another and sized to each receive a length of suture 345 therethrough. Through bore 363a is not aligned with either of apertures 363b or 363c, such that a tortuous pathway is formed once end cap 362 is assembled to suture lock 361. A hollow cylindrical connector 369 may be provided on the distal end of catheter 371 for holding locking mechanism 360 in a fixed rotational orientation relative to the catheter, as will be explained further below.

A tubular inner shaft 372 slidably disposed in catheter 371 has a lumen sized to receive two lengths of suture 345 in side-by-side relationship. At its distal end, shaft 372 is joined to suture lock 361 by a frangible joint 373 or other breakable connection. The proximal end of shaft 372 extends close to or proximally of the proximal end of catheter 371 for operation by a user independently of the user's maneuvering of the catheter. As a result of the connection between suture lock 361 and shaft 372, the sliding movement of shaft 372 relative to catheter 371 will cause locking mechanism 360 to move away from the distal end of the catheter. A pair of splines 364 on opposite sides of end cap 362 mate with a pair of notches 374 on opposite sides of connector 369 when locking mechanism 360 is in the fully retracted position, thereby assuring that the locking mechanism is properly oriented relative to catheter 371 when retracted.

Figure 11A:
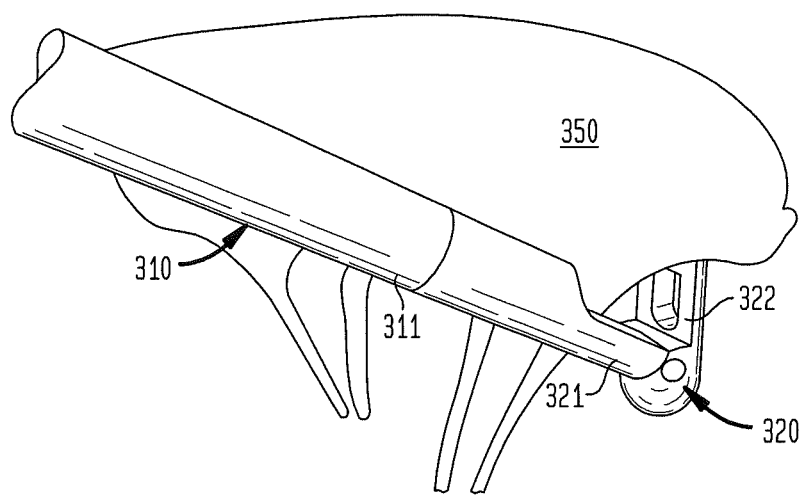
FIGS. 11A-12B are highly schematic views showing a method of repairing a heart valve leaflet using the repair device and anchors of FIGS. 9A-10B.

The use of device 310 to repair a heart valve leaflet 350 will now be described with reference to FIGS. 11, 12 and 14. Similar to the use of the devices described above, with the anchor housing tube 330 in the retracted position and jaw 322 in the closed position, repair device 310 is inserted through the vascular system of the patient until the distal end of the device, including capture tool 320, is positioned adjacent to and in front of or on the proximal side of, the heart valve leaflet tissue 350 at a first desired position. The jaw 322 is then moved to the open position, as shown in FIG. 11A, by sliding the actuation wire distally, and the repair device may be manipulated to position the open jaw behind, or on the distal side of, the leaflet tissue 350.

Figure 11B:
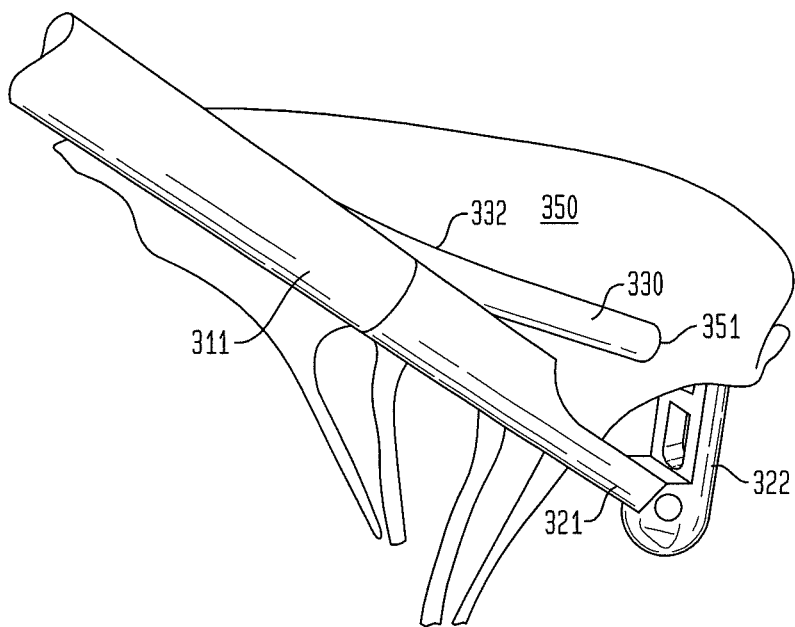
Figure 12A:
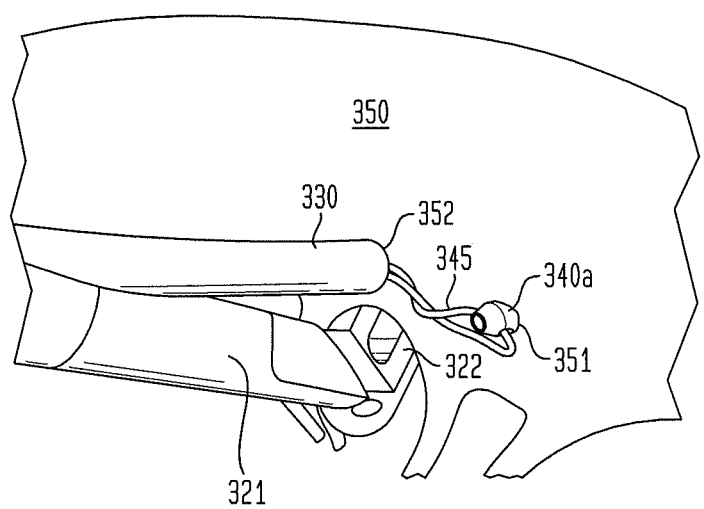
Figure 12B:
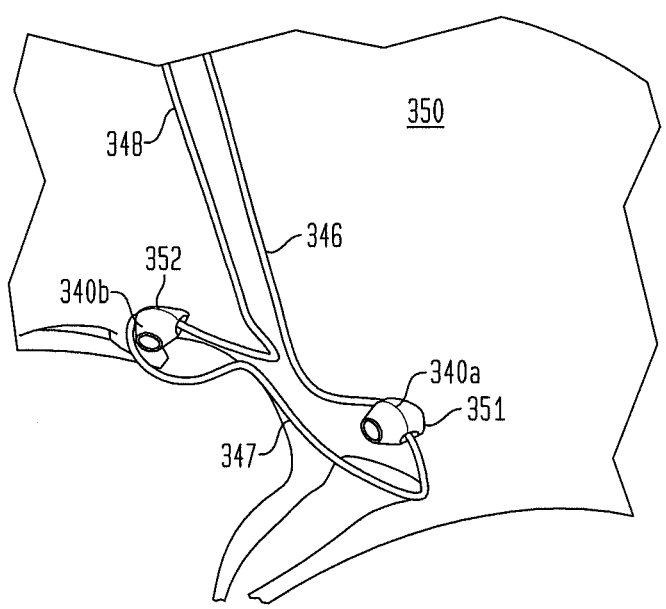

With jaw 322 positioned behind the leaflet tissue 350, the anchor housing tube 330 may be moved by the user to the extended position shown in FIG. 11B. In an alternative arrangement, the tube 330 may be biased to automatically move to the extended position as the jaw 322 is opened. In any event, as the tube 330 moves distally, the shape bias of the flexible section 332 will cause it to flex laterally away from hollow body 311. This lateral movement may be facilitated by an elongated channel 312 formed in the proximal end of fixed member 321 and in the distal portion of hollow body 311. As tube 330 continues to move distally, its distal end will eventually contact the leaflet tissue 350 at a position between the tines of fork 328. The user may then advance the pushrod 333 in the distal direction to expel a first anchor 340a from tube 330, such that the sharpened point 341 of the anchor presses against and pierces the tissue at the first desired position 351. Anchor 340a penetrates leaflet tissue 350 until the flat face 344a of body 344 contacts the surface of leaflet tissue 350, which preferably is an amount sufficient for one or more barbs 343 to become embedded within the tissue, but not enough for the sharpened point 341 to protrude from the back side of the leaflet tissue. When anchor 340a is secured to leaflet tissue 350 in this manner, the leaflet tissue can easily form around each barb to increase the grip of the anchors in the tissue, and no sharpened points 341 will be exposed such as to be able to damage any surrounding tissue. With the first anchor 340a secured to tissue 350, the suture 345 connected thereto will be located on the proximal side of the tissue, all as illustrated in FIG. 12A. The barbs 343 or other such structures on the anchor 340a inhibit the anchor from backing out of the tissue, and thus the suture is secured to the tissue at this first desired position 351. The tube 330 may then be retracted, if needed, and the jaw 322 closed before moving device 310 to a second desired position 352 at which a second anchor 340b may be deployed by repeating the procedure described above. This procedure may be repeated as many times as may be necessary to deploy the number of anchors desired. FIG. 12B illustrates the deployment of two anchors 340a and 340b, with a single suture 345 passing through the transverse apertures 342 in the anchors.

Figure 14A:
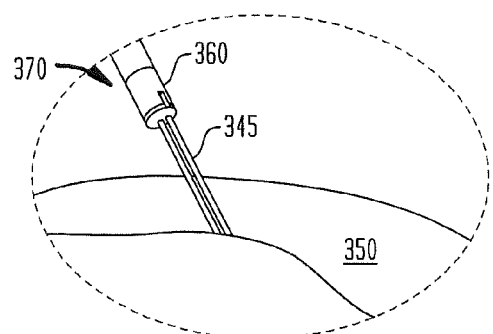
FIGS. 14A-14C are highly schematic views showing a method of repairing a heart valve leaflet using the suture lock of FIG. 13A.
Figure 14B:
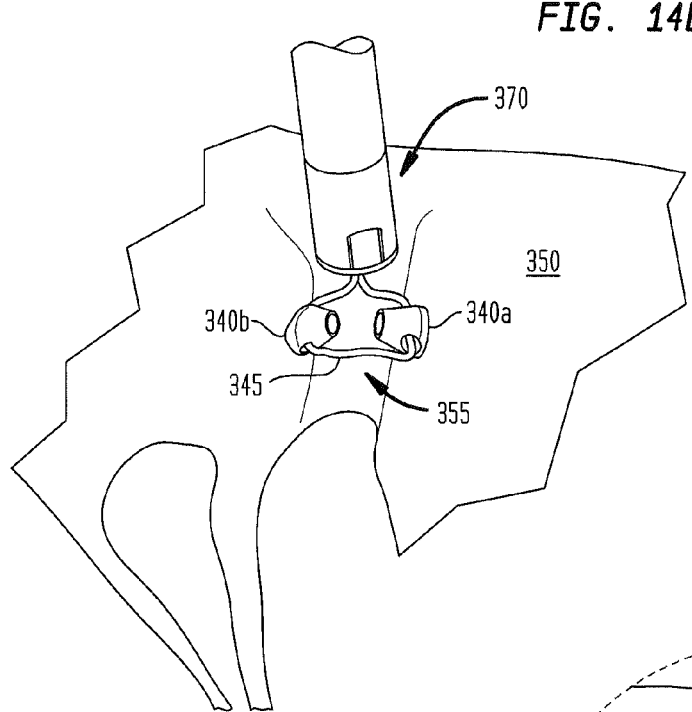
Figure 14C:
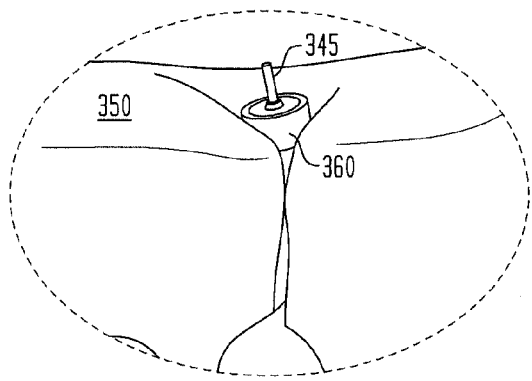

Once all of the anchors 340 have been deployed, the suture 345 may be tensioned by the user and secured to form a plicated portion 355 of the leaflet tissue 350, as illustrated in FIG. 14B. The suture 345 may be tensioned in the same manner as suture 245 is tensioned, as described above in connection with the use of device 210. Once tensioned, the suture 345 may be secured using any of the arrangements described above, such as a locking element, other cinching element or a knot, to maintain the plication of the leaflet tissue. For example, the locking element 360 on the distal end of pusher 370 may be used to secure the suture 345. Once the anchors 340 are in place in the tissue, thus providing points of securement of the suture 345 to the leaflet tissue 350, the anchor housing tube 330, and optionally the hollow body 311, may be removed from the vasculature. The suture 345 may then be assembled to the pusher 370, which subsequently may be passed through the vasculature and to the leaflet by traveling along the end portions 346 and 348 of the suture to reach the surgical site (see FIG. 14A). To assemble suture 345 to pusher 370, the end portions 346 and 348 of the suture may be threaded through apertures 363b and 363c, respectively, in end cap 362, through through bore 363a in suture lock 361, through the lumen in inner shaft 372, and out the proximal end of the inner shaft for grasping by the user (or by an operating mechanism (not shown) on the proximal end of the pusher). The suture lock 361 and end cup 362 may be only partially threaded to one another at this juncture to allow for relatively free movement of the suture 345 through the apertures in the end cup and the through bore in the suture lock. The pusher 370 may be advanced along the suture 345 until the locking mechanism 360 is adjacent the surgical site. At this point, further tension may be applied by the user to pull the anchors 340 towards one another and form the plicated portion 355 in the leaflet tissue 350. While this tension is being applied, the pusher 370 may move the locking mechanism 360 further along the suture until end cup 362 is adjacent to, and possibly even contacting, the anchors (FIGS. 14B-14C).

Once this condition is achieved, the user may rotate the inner shaft 372 relative to catheter 371 such that the suture lock 361 threads further into end cap 362 and through bore 363a in suture lock 361 moves closer to the apertures 363b and 363c in the end cap, as shown in FIG. 13B. Eventually, the portions 346 and 348 of suture 345 will become wedged between the suture lock 361 and the end cap 362, thereby locking the suture in this tensioned condition. The pusher 370 with locking mechanism 360 may be used in connection with any of the repair devices described herein.

Once the suture lock 361 bottoms out against the end cap 362 and cannot be threaded any further (either due to contact between the two components or because of the presence of the suture between the two components), the torque created by further rotation of the inner shaft 372 relative to catheter 371 will cause the frangible joint 373 between the suture lock and the inner shaft to break. With the inner shaft 372 no longer connected to suture lock 361, the inner shaft and catheter 371 may be removed simply by sliding same proximally away from locking mechanism 360. This sliding movement will disengage the splines 364 on end cap 362 from the notches 374 on connector 369 while the locking mechanism 360 remains secured to suture 345, thereby maintaining the plication in the leaflet tissue 350. Following removal of the inner shaft 372 and catheter 371, the ends of suture 345 may be cut proximally of the locking mechanism 360 and removed from the patient.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

It will be appreciated that the various dependent claims and the features set forth therein can be combined in different ways than presented in the initial claims. It will also be appreciated that the features described in connection with the individual embodiments may be shared with others of the described embodiments.

The invention claimed is:

1. A repair device for repairing a heart valve leaflet in a patient, the repair device comprising:
 an elongated hollow body having a proximal end and a distal end;
 a capture tool at the distal end of the hollow body, the capture tool being moveable between a retracted position and an extended position;

first and second tissue puncture elements at the distal end of the hollow body, each of the first and second tissue puncture elements being moveable between a retracted position and an extended position in which the first and second tissue puncture elements diverge away from one another;

at least one anchor adapted to be secured to the heart valve leaflet; and a length of suture connected to the at least one anchor.

2. The repair device of claim 1, wherein the at least one anchor has a sharpened distal tip.

3. The repair device of claim 1, wherein the tissue puncture element includes a hollow tube housing the at least one anchor.

4. The repair device of claim 3, wherein the hollow tube has a sharpened distal tip.

5. The repair device of claim 3, wherein the hollow tube has a blunt tip, and the at least one anchor has a sharpened distal tip.

6. The repair device of claim 3, further comprising a plurality of anchors adapted to be secured to the heart valve leaflet, the hollow tube housing the plurality of anchors.

7. The repair device of claim 1, wherein the tissue puncture element has an extended position projecting out from the hollow body, and a retracted position within the hollow body.

8. The repair device of claim 1, further comprising a plurality of anchors adapted to be secured to the heart valve leaflet, and a length of suture connected to each of the plurality of anchors.

9. The repair device of claim 8, wherein a single length of suture is connected to each of the plurality of anchors.

10. The repair device of claim 1, further comprising a cinching member adapted to hold the length of suture in a tensioned condition.

11. The repair device of claim 1, wherein the capture tool includes first and second jaws connected for pivotal movement relative to one another between an open position in which the second jaw is spaced apart from the first jaw, and a closed position in which the second jaw is adjacent the first jaw.

* * * * *